United States Patent

Schleicher et al.

[11] Patent Number: 5,846,297
[45] Date of Patent: Dec. 8, 1998

[54] FILTER MATERIAL AND PROCESS FOR PRODUCING $NO_2$-FREE GASES OR LIQUIDS

[75] Inventors: Andreas Schleicher, Beselich; Georg Frank, Tübingen; Wolfgang Sixl, Frankfurt, all of Germany

[73] Assignee: Ticona GmbH, Frankfurt am Main, Germany

[21] Appl. No.: 817,733

[22] PCT Filed: Oct. 13, 1995

[86] PCT No.: PCT/EP95/04036

§ 371 Date: Jun. 30, 1997

§ 102(e) Date: Jun. 30, 1997

[87] PCT Pub. No.: WO96/12551

PCT Pub. Date: May 2, 1996

[30] Foreign Application Priority Data

Oct. 25, 1994 [DE] Germany .......................... 44 37 985.4
Nov. 1, 1994 [DE] Germany .......................... 44 38 529.3

[51] Int. Cl.⁶ .................................................. B01D 53/04
[52] U.S. Cl. ................................. 95/129; 55/522; 55/528; 55/DIG. 35; 95/900; 96/153
[58] Field of Search .............................. 95/128, 129, 130, 95/900, 273; 96/108, 153, 154; 55/522, 528, DIG. 35

[56] References Cited

U.S. PATENT DOCUMENTS

| | | | |
|---|---|---|---|
| 3,577,707 | 5/1971 | White | 95/129 |
| 3,780,496 | 12/1973 | Ward, III et al. | 95/54 |
| 4,919,992 | 4/1990 | Blundell et al. | 428/131 |
| 4,933,082 | 6/1990 | Yamada et al. | 95/54 |
| 5,080,698 | 1/1992 | Krizan | 95/54 |
| 5,248,321 | 9/1993 | Yang | 95/129 |

FOREIGN PATENT DOCUMENTS

| | | |
|---|---|---|
| 0405265 | 1/1991 | European Pat. Off. . |
| 0659355 | 6/1995 | European Pat. Off. . |
| 0697236 | 2/1996 | European Pat. Off. . |
| 2904872 | 8/1980 | Germany . |
| 43 28 450 | 3/1995 | Germany . |
| 4419860 | 12/1995 | Germany . |
| 54-38287 | 3/1979 | Japan ............ 95/129 |
| 1738311 | 6/1992 | U.S.S.R. ............ 95/129 |

OTHER PUBLICATIONS

*Ullmann's Encyclopedia of Ind. Chemistry*, 5th Ed., vol. A21, VCH, Weinheim Basel, Cambridge–New York, Editor: B. Elvers, et al, 1992, pp. 605–614.

Primary Examiner—Duane S. Smith

[57] ABSTRACT

Polyarylene ethers are employed as filter material for removing $NO_2$ from gases and liquids. In the presence of an oxidizing agent having a redox potential of at least 0.96 V SHE, NO can also be removed. The filter material is used to produce $NO_2$-free gases, for example in the medical sector.

21 Claims, 1 Drawing Sheet

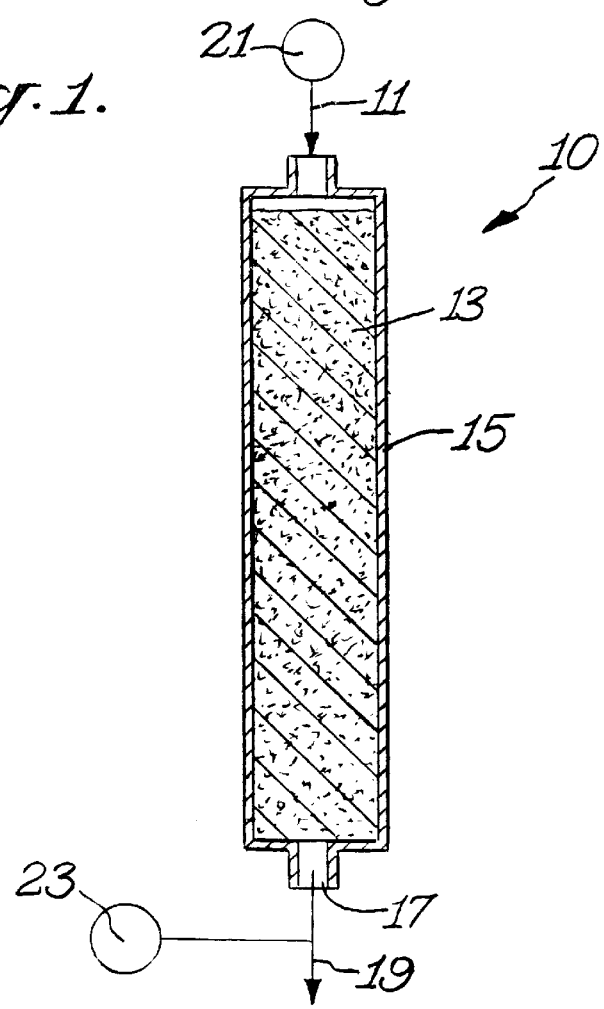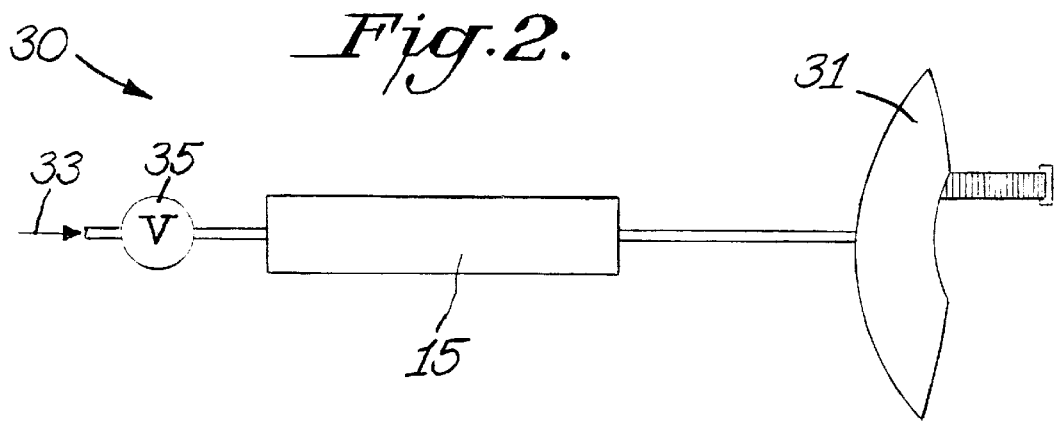

FILTER MATERIAL AND PROCESS FOR PRODUCING $NO_2$-FREE GASES OR LIQUIDS

The invention relates to a filter material, a filter and a process for producing gases and liquids which are free of nitrogen dioxide.

DESCRIPTION OF THE PRIOR ART

DE 43 28 450 A1 describes a filter material and a process for removing oxides of nitrogen from gases and liquids. Polyarylene sulfides are employed as polymeric filter material for nitrogen dioxide ($NO_2$). In the reaction of $NO_2$ with polyarylene sulfide, the sulfur groups are oxidized, reducing $NO_2$ to NO in the process.

$NO_2$-free NO gas or NO gas mixtures are required in the technology of waste-gas measurement in order to calibrate measurement and analysis systems.

Recently, the medical use of nitrogen monoxide (NO) has acquired particular importance. In the case of patients with severe pulmonary diseases, the measured addition of NO to the air supply for breathing can reduce high blood pressure in the lung circulation. In conjunction with the bronchodilatory effect of NO, this results in improved air supply to various sections of the lung, and thus to improved gas exchange as well. Important factors in this context are the exact setting of the NO content and the minimization, extending to elimination, of the $NO_2$ content. This problem occurs to an increased extent in the abovementioned application, since in said application NO is mixed with atmospheric oxygen at temperatures of around 40° C. and at high atmospheric humidity and passed over distances of about 3–6 m. During this procedure, some of the NO will be converted to $NO_2$. This leads to an increase in the $NO_2$ content of the gas, which is damaging to the patient, and to a reduction in the NO content by the amount of $NO_2$ formed. The desire here is for a converter which transforms the $NO_2$ formed back to NO, shortly before it is breathed in by the patient, but without any other alterations to the gas mixture, for example its moisture content or temperature. Compared with an $NO_2$ filter, this converter would have the advantage that there would be no change in the NO content originally set.

The colorless nitrogen monoxide (NO) reacts rapidly with molecular oxygen to form brown nitrogen dioxide ($NO_2$). In the presence of air or with ingress of air, therefore, $NO_2$ is formed from NO. Consequently, owing to the omnipresence of oxygen, $NO_2$ is an inherent impurity in NO. With the medical use of NO in particular, toxicity dictates that the content of $NO_2$ must be very low.

SUMMARY OF THE PRIOR INVENTION

It has been found that it is possible to remove $NO_2$ from gases or liquids by bringing them into contact with a polyarylene ether. Furthermore, the selective removal of $NO_2$ from NO or NO-containing media such as gases or liquids can be achieved with the aid of a polyarylene ether. Polyarylene ethers are therefore suitable filter materials for $NO_2$. This is surprising since there is a great difference in structure between the polyarylene ethers and the polyarylene sulfides, the former containing no sulfur groups.

The invention provides a filter material for removing $NO_2$ from gases and liquids, which comprises a polyarylene ether.

Furthermore, the invention provides a filter for removing $NO_2$ from gases and liquids, which comprises a polyarylene ether.

The invention additionally provides a process for producing $NO_2$-free gases or liquids, in which the gas to be purified or the liquid to be purified is brought into contact with a material which comprises a polyarylene ether.

$NO_x$ is used as a collective term for NO, $NO_2$ and $N_2O_4$.

$NO_2$ and $N_2O_4$ are in chemical equilibrium. $N_2O_4$ is removed from gases and liquids by polyarylene ethers.

The expressions "free of $NO_2$" and "quantitative removal of $NO_2$" denote that the content of $NO_2$ in a medium is less than 1 ppm.

The filter material, the filter and the process of the invention are also suitable for removing $NO_2$ from NO-containing gases or liquids.

BRIEF DESCRIPTION OF THE DRAWING

FIG. 1 of the Drawing is a schematic illustration of the use of a filter of this invention.

FIG. 2 of the Drawing is a schematic illustration of a breathing mask/filter combination of this invention, wherein the filter acts upon the intake air flow for the mask.

A polyarylene ether is a polymer which comprises at least one arylene ether unit (—A—O—; A is arylene). An arylene is an aromatic unit having two bonding sites, e.g. —$C_6H_4$—. Mono- or polycyclic aromatic compounds can form an arylene unit, such as benzene, pyridine, naphthalene, phenanthrene or anthracene. Substituted arylene units are preferred. Examples of arylene substituents are $C_1$-$C_{18}$-alkyl, such as —$CH_3$, —$C_2H_5$, —$C_3H_7$, —$C_4H_9$, —$C_5H_{11}$, —$C(CH_3)_3$, —$CH_2$—$CH(CH_3)_2$, —$C_2H_4$—$CH(CH_3)_2$ or —$CH_2$—$C(CH_3)_3$. Suitable polyarylene ethers are described in the as yet unpublished European Patent Application having the file reference 95112259.7, filing date Aug. 4, 1995, bearing the title "Filter material and process for removing ozone from gases and liquids", to which reference is made. Now EP-A 697,236

A preferred polyarylene ether is poly[2,6-dimethylphenylene oxide].

The polyarylene ether can also be mixed with one or more other polymers.

The polyarylene ether can also be a block copolymer or a blend comprising at least one polyarylene ether. Examples of suitable blends are polyarylene ether blends which comprise polystyrene homopolymer and/or polystyrene copolymer and/or polyamide and/or polyolefin.

Examples of polyarylene ethers and their preparation are given in Ullmann's Encyclopedia of Industrial Chemistry, 5th edition, volume A21, B. Elvers (Ed.), VCH, Weinheim-Basel, Cambridge-New York 1992, heading 'Poly (phenylene oxides)', page 605–614, to which reference is made.

Polyarylene ethers and polyarylene ether-containing polymers are referred to below as polymer.

The polymer can be used, for example, in the form of powders, granules, fibers, nonwovens, woven fabrics, films and/or shaped articles. The powders possess commercially customary particle sizes, with granules being a further possibility for use. The important factor in this context is that the liquid or the gas to be treated can be passed through the powder in the form, for example, of a fixed bed without hindrance. If the polymer is used as fibers, the fibers employed are staple fibers, needle felt, nonwoven material, card sliver or woven fabrics. Films or film scraps in a suitable form can also be used.

The polymer can generally be employed as unadulterated material. However, it is also possible to add fillers, such as chalk, talc, clay or mica, and/or fibrous reinforcing agents, such as glass fibers and carbon fibers, whiskers, and further additives and processing auxiliaries, for example lubricants, release agents, antioxidants and UV stabilizers.

Coatings of support materials with the polymer can be obtained by applying solutions of the polymer (examples of solvent being toluene, chloroform) to the support material. Impregnated forms are produced, for example, by impregnating an absorbent support material. The support materials employed are generally inorganic substances such as glass, silica gel, alumina, sand, ceramic compositions and metal and organic substances such as plastics.

It is also possible to apply to the polymer substances such as metals, especially noble metals and transition metals, or metal oxides such as transition metal oxides. The metals or metal oxides can be applied to the polymer, for example, by impregnation, and are then present in the form of small clusters, for example.

The process of the invention can be carried out at any temperature below the softening point of the polymers used. In general, the service temperatures are in the range from minus 10° to 200° C., preferably between 0 and 180° C.

The time required for contact of the medium to be purified with the filter material depends, inter alia, on the flow rate, the residence time, the surface area of the filter material, the geometry of the filter and the temperature. In general, the time of contact of the substituted polyarylene ether with the medium to be purified is in the range between 0.001 seconds and 10 minutes, preferably between 0.01 seconds and 1 minute. These times can also be exceeded, however.

The magnitude of the specific surface area of the polymer has a marked influence on the filter action of the polymer. The filter action of the polymer is generally greater the greater the specific surface area of the polymer. A large specific surface area and porous structures of the polymer, with a harmonized ratio of micropores to macropores proving favorable, are particularly advantageous for a filter effect. The filter effect of the polymer is also influenced by the crystallinity or, respectively, the extent of the amorphous fraction of the polymer. A high amorphous fraction in the polymer generally promotes the filter effect of the polymer.

The removal of nitrogen dioxide from gases or liquids by contact with a polyarylene ether may be based on a chemical action, catalytic action and/or physical interaction. In the case of chemical action, the polyarylene ether reacts with the nitrogen dioxide and in doing so undergoes oxidation. In the case of alkyl-substituted polyarylene ethers, the alkyl group is oxidized. This takes place with particular -readiness in the benzyl position, i.e. on the carbon atom of the alkyl group of an arylene unit which is adjacent to an aromatic nucleus.

In the removal of $NO_2$ from gases or liquids, the polymer does not form any volatile products.

The removal of $NO_2$ can be applied to $NO_x$-containing gas streams and liquids. The process of $NO_2$ removal operates, with gases for example, with a NO content of between 60% by volume and 1 ppb, preferably between 50% by volume and 10 ppb and, with particular preference, between 40% by volume and 50 ppb. The $NO_2$ content which can be separated off is between 50% by volume and 1 ppb, preferably between 20% by volume and 10 ppb and, with particular preference, between 10% by volume and 10 ppb. The ratio of NO to $NO_2$ in the liquids or gases to be treated can in this context be between 1,000,000:1 and 1:1,000,000, preferably between 10,000:1 and 1:10,000 and, with particular preference, between 1000:1 and 1:1000.

The filter can contain the polymer, for example, in the form of a powder bed, a nonwoven, a nonwoven/powder mixture, or a lattice or honeycomb structure. The powder can, however, also be incorporated into nonwovens formed from other materials.

The filter material, the filter and the process for removing $NO_2$ are suitable, for example, for producing $NO_2$-free NO gas or $NO_2$-free NO-containing gas for analytical gases and, in particular, for NO applications in medicine, for example in the case of patients with severe pulmonary diseases, the measured addition of NO to the air supply for breathing can reduce high blood pressure in the lung circulation. This applies to patients both with IRDS (Infant Respiratory Distress Syndrome) and those with ARDS (Adult Respiratory Distress Syndrome). Also conceivable, however, are applications in cardiac surgery, for the intensive artificial respiration of patients with NO in order to reduce high blood pressure in the pulmonary circulation. Important factors for these applications include both the exact setting of the NO content and the minimization, extending to elimination, of the $NO_2$ content.

Owing to the harmfulness of $NO_2$ to humans, the formation of $NO_2$ from NO and oxygen in medical applications of NO, which employ mixtures of NO and oxygen at elevated temperature (e.g. 40° C.) and as a moisture-containing gas, is a great problem. The use of the process or filter of the invention for removing $NO_2$ can eliminate this problem. $NO_2$ produced between filter and lung can no longer be removed. The distance between filter and lung should therefore be as short as possible.

The process and the filter for $NO_2$ removal can be employed, in medical technology, at a number of points in an artificial respiration system. The filter can be accommodated directly behind the pressure reduction valve in order to minimize the proportion of $NO_2$ which is formed or which remains during the production of the NO/nitrogen gas mixture used. Using the process described herein, it is possible to purify gas mixtures which contain NO in a concentration of between 1 ppb and 100,000 ppm in nitrogen, preferably from 1 ppm to 10,000 ppm. In this context, the volume flow of the NO/nitrogen gas mixture can be between 0.001 and 1000 l/min, preferably between 0.01 and 250 l/min.

In the case of treatment involving NO uptake via the lung, the NO-containing gas and the added air can be purified upstream of or in the filter, with the result that an $NO_2$-free gas mixture is inhaled. In this case the filter can, for example, consist of a breathing mask, with the filter containing the polymer being inserted in the intake air flow of the mask.

When the polymer comes into contact with nitrogen dioxide, nitrogen monoxide is sometimes produced. The filter effect of the polymer with respect to nitrogen monoxide is negligible. Nevertheless, nitrogen monoxide as well can be removed quantitatively if at least one oxidative inorganic or organic compound which has a redox potential of at least 0.96 V against the standard hydrogen electrode (SHE) is added to the polymer or filter material, examples of such compounds being chlorinated lime, sodium hypochlorite, vanadium pentoxide or dichlorodicyanoquinone. These oxidizing agents convert the NO into $NO_2$. By using a suitable oxidizing agent in combination with a polyarylene ether, the filter material, the filter and the process are also suitable for removing NO from gases and liquids.

The invention additionally provides, therefore, a filter material and a filter for removing NO and $NO_2$ from gases and liquids, the filter material or the filter comprising a polyarylene ether and an oxidizing agent having a redox potential of at least 0.96 V SHE.

The invention additionally provides a process for producing NO-free and $NO_2$-free gases or liquids, which comprises bringing the gas to be purified or the liquid to be purified into contact with an oxidizing agent having a redox potential of at least 0.96 V SHE and with a material which comprises a polyarylene ether.

The filter material, the filter and the process for removing NO and/or $NO_2$ can be employed with all liquids and gases which contain oxides of nitrogen. They can be employed, for example, in filter masks, in air-conditioning systems, in automobiles (e.g. air filters, exhaust filters), for removing nitrogen oxides produced in combustion (e.g. flue-gas purification), and also for removing and detoxifying oxides of nitrogen in liquids.

Polyarylene ethers can also be employed as a suspension or solution for removing NO and/or $NO_2$ from gases. For example, suspensions of polyarylene ether may consist of finely divided polyarylene ether in water. Solutions of polyarylene ethers can be prepared, for example, with aromatic solvents such as toluene or nonaromatic solvents such as chloroform. For removing oxides of nitrogen, a gas to be purified is passed through the liquid.

The removal of NO and/or $NO_2$ from a liquid can, for example, involve the polymer being suspended in the liquid (extractive stirring method) or being passed through a column which is packed with the polymer (column method).

It is advantageous for the removal of $NO_2$ or NO from a gas or a liquid to use a filter material having a large surface area, for example a porous powder or a porous fiber.

DETAILED DESCRIPTION

Turning now to FIG. 1 of the Drawing, a preferred embodiment of system 10 for utilizing a filter cartridge 15 of this invention includes, on the cartridge-inlet side, a gas mixing system and flow control system 21 wherein a commercial analytical gas mixture containing a minor amount of $NO_2$ (e.g. 538 ppm) and synthetic air is diluted, so that the $NO_2$ content of the resulting gas stream 11 is decreased and/or the pressure of gas stream 11 is controlled (flow control system 21 can include a pressure reduction valve). Gas stream 11 is passed through cartridge 15, which is packed with a filter material 13 comprising a poly(phenylene oxide) such as poly-para[2,6-dimethylphenylene oxide]. The filter material 13 can be particulate, e.g. in the form of finely ground granules. The gas stream 19 which has passed through cartridge 15 is analyzed, on the gas-outlet side 17, by a suitable measuring instrument for both NO and $NO_2$ content, e.g. an $NO/NO_2$ chemoluminescence device 23 which can detect <1 ppm of either of these gases. The content of $NO_2$ (and optionally NO) in gas stream 19 can thereby measured over a period time, e.g. several hours.

FIG. 2 illustrates how the filter cartridge 15 of FIG. 1 can be utilized in an artificial respiration system 30 comprising a breathing mask 31, filter 15, and pressure reduction valve 35, filter 15 purifies the intake air flow 33 upstream of mask 31, so that an essentially $NO_2$-free gas mixture can be inhaled from breathing mask 31. The pressure reduction valve 35 controls the volume flow so that it will be in the range of 0.001 to 1000 l/min, preferably between 0.01 and 250 l/min.

EXAMPLES

1) A gas mixture of 100 ppm of $NO_2$ with nitrogen was produced in a gas mixing system consisting of flow controllers (type 1259C) and the corresponding control instrument (type 247C, both from MKS Instruments, 81829 Munich, Federal Republic of Germany) by diluting a commercial analytical gas mixture (538 ppm of $NO_2$ in synthetic air, Messer Griesheim GmbH, Specialty Gases Plant, 47009 Duisburg, Federal Republic of Germany) and was passed at room temperature (25° C.) through a filter cartridge packed with poly-para[2,6-dimethylphenylene oxide], abbreviated to PPO, in the form of finely ground granules (average particle diameter $D_{50}$: about 50 μm). The absorption path is characterized by the following parameters:

| | |
|---|---|
| Internal diameter of the filter cartridge: | 2 cm |
| Mass of PPO employed: | 15 g |
| Height of PPO bed: | 9 cm |
| Gas throughput: | 25 l/h |
| Gas flow rate: | 2.2 cm/s |

After passing through the filter cartridge, the gas was analyzed for its content of NO and $NO_2$ by passing it into an $NO/NO_2$ chemoluminescence measuring instrument (type CLD 700 El Ht, Eco Physics AG, Durnten, Switzerland; minimum detection limit 0.1 ppm, linearity ±1% end-scale deflection) with the measurement range setting 0–100 ppm. The filter action for $NO_2$ starts straight away. Within a period of 2 hours, the $NO_2$ concentration was below the detection limit of 1 ppm. For a further 18 hours, the concentration of $NO_2$ remained below the MAC value of 5 ppm.

2) A gas mixture of 500 ppm of $NO_2$ in synthetic air was passed as in Example 1 (measurement range 0–1000 ppm) through a filter cartridge and analyzed. The absorption path is characterized by the following parameters:

| | |
|---|---|
| Internal diameter of the filter cartridge: | 2 cm |
| Mass of PPO employed: | 5 g |
| Height of PPO bed: | 3 cm |
| Gas throughput: | 48 l/h |
| Gas flow rate: | 4.25 cm/s |

The filter was fed with gas until the concentration of $NO_2$ passed through was about 80% of the initial concentration. The filter capacity calculated from this was 18% (percent by weight) based on $NO_2$ 3) With a gas mixture with 500 ppm of $NO_2$ in helium, produced as in Example 1 (but with an analytical gas mixture comprising 600 ppm of $NO_2$ in helium; measurement range 0–1000 ppm), the concentration of $NO_2$ remained below the detection limit for 20 minutes. After 16 hours, 40 ppm were measured, i.e. after this time the filter still has an efficiency of more than 90%.

4) A gas mixture of 500 ppm of $NO_2$ in synthetic air was passed as in Example 1 at room temperature (25° C.) through a filter cartridge which was packed with a polyarylene ether (Blendex XHPP 820, GE Plastics, U.S.A.) in granular form (average particle diameter about 500–800 μm) The absorption path is characterized by the following parameters:

| | |
|---|---|
| Internal diameter of the filter cartridge: | 2 cm |
| Mass of PPO employed: | 5 g |
| Height of PPO bed: | 4.5 cm |
| Gas throughput: | 48 l/h |
| Gas flow rate: | 4.25 cm/s |

At the beginning of the experiment, the $NO_2$ concentration remained below the detection limit for 5 minutes. After 3 hours, 75 ppm of $NO_2$ were able to pass through the filter (measurement range 0–1000 ppm).

We claim:

1. A filter material for removing NO and $NO_2$ from gases or liquids, comprising a polyarylene ether and an oxidizing agent having a redox potential of at least 0.96 V SHE.

2. A filter for treating an $NO_x$ containing gas, wherein $NO_x$ includes $NO_2$, comprising a filter cartridge and, contained therein, a filter material which is constructed and arranged to decrease the amount of $NO_2$ in said $NO_x$-containing gas, said filter material comprising a filter material as claimed in claim 1.

3. An artificial respiration system for providing a gas mixture flow, said system comprising a pressure reduction valve, for providing a gas mixture flow of from 0.001 to 1000 l/min, and a filter as claimed in claim 2.

4. An artificial respiration system as claimed in claim 3, wherein said system includes a breathing mask, and said filter cartridge is arranged to be upstream of the breathing mask.

5. A filter comprising a filter cartridge and, contained therein, a filter material of claim 1.

6. A filter as claimed in claim 2, wherein the filter material comprises a polyarylene ether having polyarylene ether units of the formula —Ar—O—, wherein Ar is a monocyclic aromatic group having two bonding sites.

7. A filter as claimed in claim 6, wherein said monocyclic aromatic group is benzene or pyridine which is unsubstituted or is substituted with at least one $C_1$–$C_{18}$-alkyl.

8. A filter as claimed in claim 7, wherein said aromatic group is 2,6-dimethylphenylene.

9. An artificial respiration system as claimed in claim 3, wherein the filter contains a polyarylene ether having an arylene unit of the formula —Ar—O—, wherein Ar is benzene or pyridine which is unsubstituted or substituted with at least one $C_1$–$C_{18}$-alkyl.

10. A filter material as claimed in claim 1, wherein the material comprises a polyarylene ether having an arylene unit of the formula —Ar—O—, wherein Ar is benzene or pyridine which is unsubstituted or substituted with at least one $C_1$–$C_{18}$-alkyl.

11. A process for treating an $NO_x$-containing gas or liquid, wherein $NO_x$ includes $NO_2$, to decrease the amount of $NO_2$ therein, which comprises bringing the gas or liquid to be treated into contact with a material which comprises a polyarylene ether, and wherein the amount of $NO_2$ in said gas or liquid to be treated ranges from 1 ppb to 50 volume %.

12. The process as claimed in claim 11, wherein the gas or liquid to be treated reacts chemically with the polyarylene ether.

13. The process as claimed in claim 12, wherein the polyarylene ether is not converted to a volatile product.

14. The process as claimed in claim 11, wherein the gas or liquid to be treated contains oxygen.

15. The process as claimed in claim 11, wherein the gas or liquid to be treated contains nitrogen or air.

16. The process as claimed in claim 11, wherein the $NO_2$ of said gas or liquid to be treated is in equilibrium with $N_2O_4$.

17. The process as claimed in claim 11, wherein the polyarylene ether has arylene ether units of the formula —Ar—O—, and wherein Ar is benzene or pyridine which is unsubstituted or substituted with at least one $C_1$–$C_{18}$-alkyl.

18. The process as claimed in claim 17, wherein said polyarylene ether comprises poly(2,6-dimethylphenylene oxide).

19. The process as claimed in claim 11 wherein the amount of NO in said gas or liquid to be treated ranges from 1 ppb to 60 volume %.

20. The process as claimed in claim 11, wherein said gas or liquid to be treated contains both NO and $NO_2$, and wherein the amounts of both NO and $NO_2$ are decreased by bringing the gas or liquid to be treated into contact with a polyarylene ether and an oxidizing agent having a redox potential of at least 0.96 V SHE.

21. A method for improving the lung function of a patient comprising the steps of:

providing a flow of lung function-improving gas containing oxygen and NO and at least the inherent content of $NO_2$ resulting from oxidation of NO, and selectively decreasing the amount of $NO_2$ in said lung function-improving gas by bringing said flow of lung function-improving gas into contact with a polyarylene ether before delivering said gas to a patient.

* * * * *